(12) United States Patent
Jähne et al.

(10) Patent No.: US 6,329,407 B1
(45) Date of Patent: *Dec. 11, 2001

(54) USE OF POLYCYCLIC THIAZOLE SYSTEMS FOR THE TREATMENT OF OBESITY

(75) Inventors: Gerhard Jähne; Karl Geisen, both of Frankfurt; Hans-Jochen Lang, Hofheim; Martin Bickel, Bad Homburg, all of (DE)

(73) Assignee: AventisPharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/500,463

(22) Filed: Feb. 9, 2000

(30) Foreign Application Priority Data

Feb. 26, 1999 (DE) ............................... 199 08 535

(51) Int. Cl.⁷ .................................................. A61K 31/425
(52) U.S. Cl. .............................................................. 514/366
(58) Field of Search ............................................. 514/366

(56) References Cited

U.S. PATENT DOCUMENTS

| | | | |
|---|---|---|---|
| 5,360,803 | 11/1994 | Shishido et al. | 514/224.2 |
| 6,187,801 * | 2/2001 | Jahne et al. | 514/366 |

FOREIGN PATENT DOCUMENTS

| | | |
|---|---|---|
| 199 08 533 | 8/2000 | (DE) . |
| 0 666 263 | 8/1995 | (EP) . |
| 0 749 966 | 12/1996 | (EP) . |
| 0 749 966 A1 | 12/1996 | (EP) . |

OTHER PUBLICATIONS

P. Tyle, "Iontophoretic Devices for Drug Delivery", PHarmaceutical Research, 1986, 3 (6) : pp. 318–326.

N. Miyaura et al., "Palladium–Catalyzed Cross–Coupling Reactions of Organoboron Compounds ", Chem. Rev., 1995, 95, pp. 2457–2483.

Takayuki Oh–e et al., "Palladium–Catalyzed Cross–Coupling Reaction of Organoboron Compounds with Organic Triflates", Org. Chem., 1993, 58, pp. 2201–2208.

K. Sonagashira et al., "Convenient Synthesis of Acetylenes: Catalytic Substitutions of Acetylenic Hydrogen with Bromoalkenes, Iodoarenes, and Bromopyridines", 1975, Tetrahedron Lett., pp. 4467–4470.

S. Takahashi et al., "A Convenient Synthesis of Ethynylarenes and Diethynylarenes", 1980, Synthesis, pp. 627–630.

E. Negishi et al., "Direct Synthesis of Terminal Alkynes via Pd–Catalyzed Cross coupling of Aryl and Alkenyl Halides with Ethynylmetals Containing Zn, Mg, and Sn. Critical Comparison of Countercations", 1997, J. Org. Chem., 62, pp. 8957–8960.

A. Hassner et al., "Charge–shift Probes of Membrane Potential. Synthesis", 1984, J. Org. Chem., 49, pp. 2546–2551.

* cited by examiner

Primary Examiner—Frederick Krass
Assistant Examiner—Donna Jagoe
(74) Attorney, Agent, or Firm—Heller, Ehrman, White & McAuliffe , LLP

(57) ABSTRACT

The invention relates to the use of polycyclic thiazole systems and their physiologically tolerated salts and physiologically functional derivatives for the treatment of obesity.

The treatment involves administration of a compound of formula I,

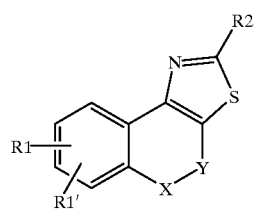

in which the radicals have the stated meanings, and of their physiologically tolerated salts and physiologically functional derivatives.

22 Claims, No Drawings

USE OF POLYCYCLIC THIAZOLE SYSTEMS FOR THE TREATMENT OF OBESITY

BACKGROUND OF THE INVENTION

The invention relates to the use of polycyclic thiazole systems and of their physiologically tolerated salts and physiologically functional derivatives for producing therapeutic agents for the treatment of obesity.

EP 0 749 966 describes polycyclic thiazole systems with 5-HT$_3$ receptor agonistic properties as active ingredients for treating CNS disorders.

The invention was based on the object of providing compounds which display a therapeutically utilizable anorectic effect.

SUMMARY OF THE INVENTION

The invention relates to a method for the treatment of obesity comprising administering to a patient in need of such treatment a pharmaceutical composition comprising a pharmaceutically acceptable carrier and a compound of formula I:

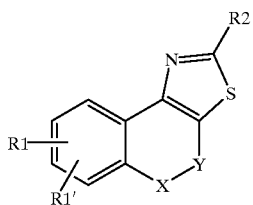

in which

Y is CH$_2$ or CH$_2$—CH$_2$;

X is a direct linkage, CH$_2$, O, NR3 or S;

R1, R1' are independently H, F, Cl, Br, I, CF$_3$, CN, COOH, COO(C$_1$-C$_6$)alkyl, CONH$_2$, CONH(C$_1$-C$_6$)alkyl, CON[(C$_1$-C$_6$)alkyl]$_2$, (C$_1$-C$_6$)-alkyl, (C$_2$-C$_6$)-alkenyl, (C$_2$-C$_6$)-alkynyl, OCF$_3$, O—(C$_2$-C$_6$)-alkyl (where one, more than one or all hydrogen(s) in the alkyl, alkenyl and alkynyl radicals may be replaced by fluorine, or one hydrogen may be replaced by OH, CN, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-phenyl, SO$_2$—(C$_1$-C$_6$)-alkyl, SO—(CH$_2$)-phenyl, SO$_2$—(CH$_2$)$_n$-phenyl (where n is 0–6 and the phenyl radical may be substituted up to two times by F, Cl, Br, OH, CF$_3$, NO$_2$, CN, OCF$_3$, O—(C$_1$-C$_6$)-alkyl, (C$_1$-C$_6$)-alkyl or NH$_2$), NH$_2$, NH—(C$_1$-C$_6$)-alkyl, N((C$_1$-C$_6$)-alkyl)$_2$, NH(C$_1$-C$_7$)-acyl, phenyl, biphenylyl, (O—CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be optionally substituted up to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is (C$_1$-C$_8$)-alkyl, (C$_3$-C$_7$)-cycloalkyl, (C$_2$-C$_6$)-alkenyl, (C$_2$-C$_6$)-alkynyl, C(CN)=C(CH$_3$)$_2$, C(O)OCH$_2$CH$_3$, CH$_2$—O—C(O)—C(CH$_3$)$_3$, (C$_4$-C$_7$) cycloalkenyl (where one, more than one or all hydrogen(s) in the alkyl, alkenyl or alkynyl radicals may be replaced by fluorine, or one hydrogen may be replaced by OH, CN or O—(C$_1$-C$_4$)-alkyl), (CH$_2$)$_n$—NR6R7 (where n is 1–6 and R6 and R7 are independently H, (C$_1$-C$_6$)-alkyl, (C$_3$-C$_6$)-cycloalkyl, CO—(C$_1$-C$_6$)-alkyl, CHO or CO-phenyl or —NR6R7 is a ring selected from the group consisting of pyrrolidine, piperidine, morpholine, piperazine, 4-methylpiperazin-1-yl, 4-benzylpiperazin-1-yl and phthalimidyl) or (CH$_2$)$_n$-aryl (where n is 0–6 and aryl is selected from the group consisting of phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 1,3,5-triazin-2-yl, 2- or 5-benzimidazolyl, 2-benzothiazolyl, 1,2,4-triazol-3-yl, 1,2,4-triazol-5-yl, tetrazol-5-yl, indol-3-yl, indol-5-yl and N-methylimidazol-2-, -4- or -5-yl, wherein the aryl radical or heteroaryl radical may be substituted up to two times by F, Cl, Br, OH, CF$_3$, NO$_2$, CN, OCF$_3$, O—(C$_1$-C$_6$)-alkyl, S—(C$_1$-C$_6$)-alkyl, SO—(C$_1$-C$_6$)-alkyl, SO$_2$—(C$_1$-C$_6$)-alkyl, (C$_1$-C$_6$)-alkyl, (C$_3$-C$_6$)-cycloalkyl, COOH, COO(C$_1$-C$_6$)alkyl, COO(C$_3$-C$_6$) cycloalkyl, CONH$_2$, CONH(C$_1$-C$_6$)alkyl, CON[(C$_1$-C$_6$)alkyl]$_2$, CONH(C$_3$-C$_6$)cycloalkyl, NH$_2$, NH—CO—(C$_1$-C$_6$)-alkyl, NH—CO-phenyl, pyrrolidin-1-yl, morpholin-1-yl, piperidin-1-yl, piperazin-1-yl, 4-methylpiperazin-1-yl, (CH$_2$)$_n$-phenyl, O—(CH$_2$)$_n$-phenyl, S—(CH$_2$)$_n$-phenyl or SO$_2$—(CH$_2$)$_n$-phenyl, where n=0–3);

R3 is H, (C$_1$-C$_6$)-alkyl, CO—(C$_1$-C$_5$)-alkyl, CO—(C$_3$-C$_6$)-cycloalkyl, SO$_2$-phenyl or p-toluenesulfonyl;

and their physiologically tolerated salts and physiologically functional derivatives.

DETAILED DESCRIPTION OF THE PREFERRED EMBODIMENTS

The present invention is directed to a method of treating obesity which encompasses prophylaxis and amelioration of obesity comprising administering to a patient in need thereof a pharmaceutical composition comprising a compound of of formula I:

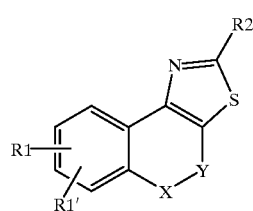

in which

Y is CH$_2$ or CH$_2$—CH$_2$;

X is a direct linkage, CH$_2$, O, NR3 or S;

R1, R1' are independently H, F, Cl, Br, I, CF$_3$, CN, COOH, COO(C$_1$-C$_6$)alkyl, CONH$_2$, CONH(C$_1$-C$_6$) alkyl, CON[(C$_1$-C$_6$)alkyl]$_2$, (C$_1$-C$_6$)-alkyl, (C$_2$-C$_6$)-alkenyl, (C$_2$-C$_6$)-alkynyl, OCF$_3$, O—(C$_2$-C$_6$)-alkyl (where one, more than one or all hydrogen(s) in the alkyl, alkenyl and alkynyl radicals may be replaced by fluorine, or one hydrogen may be replaced by OH, CN, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO$_2$—(C$_1$–C$_6$)-alkyl, SO—(CH$_2$)-phenyl, SO$_2$—(CH$_2$)$_n$-phenyl (where n is 0–6 and the phenyl radical may be substituted up to two times by F, Cl, Br, OH, CF$_3$, NO$_2$, CN, OCF$_3$, O—(C$_1$–C$_6$)-alkyl, (Cl-C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6 ), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is (C$_1$–C$_8$)-alkyl, (C$_3$–C$_7$)-cycloalkyl, (C$_2$–C$_6$)-alkenyl, (C$_2$–C$_6$)-alkynyl, C(CN)=C(CH$_3$)$_2$, C(O)OCH$_2$CH$_3$, CH$_2$—O—C(O)—C(CH$_3$)$_3$, (C$_4$–C$_7$) cycloalkenyl (where one, more than one or all hydrogen(s) in the alkyl, alkenyl and alkynyl radicals may be replaced by fluorine, or one hydrogen may be replaced by OH, CN or O—(C$_1$–C$_4$)-alkyl), (CH$_2$)$_n$—NR6R7 (where n is 1–6 and R6 and R7 are independently H, (C$_1$–C$_6$)-alkyl, (C$_3$–C$_6$)-cycloalkyl, CO—(C$_1$–C$_6$)-alkyl, CHO or CO-phenyl or —NR6R7 is a ring selected from the group consisting of pyrrolidine, piperidine, morpholine, piperazine, 4-methylpiperazin-1-yl, 4-benzylpiperazin-1-yl and phthalimidyl) or (CH$_2$)$_n$-aryl (where n is 0–6 and aryl is selected from the group consisting of phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 1,3,5-triazin-2-yl, 2- or 5-benzimidazolyl, 2-benzothiazolyl, 1,2,4-triazol-3-yl, 1,2,4-triazol-5-yl, tetrazol-5-yl, indol-3-yl, indol-5-yl and N-methylimidazol-2-, -4- or -5-yl, wherein the aryl radical or heteroaryl radical may be optionally substituted up to two times by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO (C$_3$–C$_6$)cycloalkyl, CONH$_2$, CONH(C$_1$–C$_6$)alkyl, CON[(C$_1$–C$_6$)alkyl]$_2$, CONH(C$_3$–C$_6$)cycloalkyl, NH$_2$, NH—CO—(C$_1$–C$_6$)-alkyl, NH—CO-phenyl, pyrrolidin-1-yl, morpholin-1-yl, piperidin-1-yl, piperazin-1-yl, 4-methylpiperazin-1-yl, (CH$_2$)$_n$-phenyl, O—(CH$_2$)$_n$-phenyl, S—(CH$_2$)$_n$-phenyl or SO$_2$—(CH$_2$)$_n$ -phenyl, where n=0–3);

R3 is H, (C$_1$–C$_6$)-alkyl; CO—(C$_1$–C$_5$)-alkyl, CO—(C$_3$–C$_6$)-cycloalkyl, SO$_2$-phenyl or p-toluenesulfonyl;

and their physiologically tolerated salts and physiologically functional derivatives.

A preferred embodiment encompasses treating obesity with a pharmaceutical composition comprising a compound of formula I wherein:

Y is CH$_2$;

X is a direct linkage or CH$_2$;

R1, R1' are independently H, F, Cl, Br, I, CF$_3$, CN, COOH, COO(C$_1$–C$_6$)alkyl, CONH$_2$, CONH(C$_1$–C$_6$) alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, OCF$_3$, O—(C$_2$–C$_6$)-alkyl (where one, more than one or all hydrogen(s) in the alkyl, alkenyl and alkynyl radicals may be replaced by fluorine, or one hydrogen may be replaced by OH, CN or NH$_2$), NH$_2$, NH—(C$_1$–C$_6$)-alkyl, N((C$_1$–C$_6$)-alkyl)$_2$, phenyl, O—(CH$_2$)$_n$-phenyl (where n is 0–6 ), 1- or 2-naphthyl, 2-, 3- or 4-pyridyl, 2- or 3-furanyl or 2- or 3-thienyl (wherein the phenyl, naphthyl, pyridyl, furanyl or thienyl rings may be optionally substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$);

R2 is (C$_1$–C$_8$)-alkyl, (C$_3$–C$_7$)-cycloalkyl, (C$_2$–C$_6$)-alkenyl, (C$_2$–C$_6$)-alkynyl, C(CN)=C(CH$_3$)$_2$, C(O)OCH$_2$CH$_3$, CH$_2$—O—C(O)—C(CH$_3$)$_3$, (C$_4$–C$_7$)-cycloalkenyl (where one, more than one or all hydrogen(s) in the alkyl, alkenyl or alkynyl radicals may be replaced by fluorine, or one hydrogen may be replaced by OH, CN or O—(C$_1$–C$_4$)-alkyl), (CH$_2$)$_n$—NR6R7 (where n is 1–6, and R6 and R7 are independently H, (C$_1$–C$_6$)-alkyl, (C$_3$–C$_6$)-cycloalkyl, CO—(C$_1$–C$_6$)-alkyl, CHO or CO-phenyl) or (CH$_2$)$_n$-aryl (where n is 0–6 , and aryl is selected from the group consisting of phenyl, biphenylyl, 1- or 2-naphthyl, 2-, 3- or 4-pyridyl, benzothiazol-2-yl, indol-3-yl, indol-5-yl, 2- or 3-furanyl and 2- or 3-thienyl, wherein the phenyl, biphenylyl, naphthyl, pyridyl, furanyl or thienyl rings may be optionally substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$-C$_6$)-alkyl, or CONH$_2$), and their physiologically tolerated salts and physiologically functional derivatives.

A particularly preferred embodiment encompasses treating obesity with a pharmaceutical composition comprising a compound of formula I wherein:

Y is —CH$_2$—;

X is —CH$_2$— or a direct linkage;

R1 is Cl, Br, (C$_1$–C$_6$)-alkyl, OCF$_3$ or O—(C$_2$–C$_6$)-alkyl (where one, more than one or all hydrogen(s) in the alkyl radicals may be replaced by fluorine) or phenyl which may be substituted up to 3 times by F, Cl, Br, OH or (C$_1$–C$_6$)-alkyl);

R1' is H or R1;

R2 is (C$_1$–C$_6$)-alkyl, (C$_1$–C$_6$)-alkyl-CN, C(CN)=C(CH$_3$)$_2$, C(O)OCH$_2$CH$_3$, CH$_2$—O—C(O)—C(CH$_3$)$_3$) or (CH$_2$)$_n$-aryl (where n is 0–2 and aryl is selected from the group consisting of phenyl, 2-, 3-or 4-pyridyl, benzothiazol-2-yl, indol-3-yl and indol-5-yl and wherein the aryl radical or heteroaryl radical may be substituted up to two times by F, Cl, Br, OH, CF$_3$, NO$_2$, CN, OCF$_3$, (C$_1$–C$_6$)-alkyl or O—(C$_1$–C$_6$)-alkyl);

and their physiologically tolerated salts.

The method of treatment contemplated encompasses not only treatment by administration of a pharmaceutical composition which comprises a compound of formula (I) and a pharmaceutically acceptable carrier but also administration of the compound of formula (I) absent a pharmaceutically acceptable carrier.

The invention also relates to the use of compounds of formula I in the form of their racemates, racemic mixtures and pure enantiomers, and to their diastereomers and mixtures thereof.

The alkyl, alkenyl and alkynyl radicals in the substituents R1, R1', R2 and R3 may be either straight-chain or branched.

Pharmaceutically acceptable salts are particularly suitable for medical applications because of their greater solubility in water compared with the initial compounds on which they are based. These salts must have a pharmaceutically acceptable anion or cation. Suitable pharmaceutically acceptable acid addition salts of the compounds of the formula I are salts of inorganic acids such as hydrochloric acid, hydrobromic acid, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. It is particularly preferred to use the chloride for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in non-therapeutic, for example in vitro, applications.

The term "physiologically functional derivative" used herein refers to any physiologically tolerated derivative of a compound according to the invention, for example an ester, which is able on administration to a mammal, such as, for example, to humans, to form (directly or indirectly) such a compound or an active metabolite thereof.

A further aspect of this invention is the use of prodrugs of compounds of the formula I. Such prodrugs may be metabolized in vivo to a compound of the formula I. These prodrugs may themselves be active or not.

The compounds of the formula I may also exist in various polymorphous forms, for example as amorphous and crystalline polymorphous forms. All polymorphous forms of the compounds of the formula I fall within the scope of the invention and are a further aspect of the invention.

All references hereinafter to "compound(s) of the formula (I)" refer to compound(s) of the formula (I) as described above and to the salts, solvates and physiologically functional derivatives thereof as described herein.

The compounds of formula (I) are used in the treatment of obesity. Treatment of obesity encompasses prophylaxis and amelioration of obesity. The treatment regiment involves administering an obesity treating effective amount of a compound of formula (I) as part of a pharmaceutical composition.

The amount of a compound of the formula (I), which is an "effective amount," that is necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram body weight, for example 3–10 mg/kg/day. An intravenous dose may be, for example, in the range from 0.3 mg to 1.0 mg/kg, which may suitably be administered as infusion of 10 ng to 100 ng per kilogram and per minute. Infusion solutions suitable for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single dose formulations which may be administered orally, such as, for example, tablets or capsules, may contain, for example, from 1.0 to 1000 mg, typically from 10 to 600 mg. In the case of pharmaceutically acceptable salts, the above weight data are based on the weight of the aminothiazole ion derived from the salt. The compounds of the formula (I) may be used for treatment of obesity as the compound itself, but they are preferably in the form of a pharmaceutical composition with a pharmaceutically acceptable carrier. The carrier must, of course, be compatible in the sense of compatibility with other ingredients of the composition and not be harmful to the patient's health. The carrier may be a solid or a liquid or both and is preferably formulated with the compound as single dose, for example as tablet, which may contain from 0.05% to 95% by weight of the active ingredient. Further pharmaceutically active substances may likewise be present, including further compounds of the formula (I). The pharmaceutical compositions according to the invention may be produced by one of the known pharmaceutical methods which essentially consists of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of the formula (I) used in each case. Coated formulations and coated slow-release formulations also fall within the scope of the invention. Acid- and gastric fluid-resistant formulations are preferred. Suitable gastric fluid-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, pastilles or tablets, each of which contains a defined amount of the compound of the formula (I); as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the pharmaceutically acceptable carrier (which may consist of one or more additional ingredients) are brought into contact. In general, the compositions are produced by uniform and homogeneous mixing of the active ingredient with a liquid and/or finely dispersed solid carrier, after which the product is shaped if necessary. Thus, for example, a tablet may be produced by compressing or shaping the powder or granules of the compound, where appropriate with one or more additional ingredients. Compressed tablets may be produced by tabletting the compound in free-flowing form, such as, for example, a powder or granules, where appropriate mixed with a binder, lubricant, inert diluent and/or one (or more) surface-active/dispersing agents in a suitable machine. Shaped tablets may be produced by shaping, in a suitable machine, the compound which is in powder form and has been moistened with an inert liquid diluent.

Pharmaceutical compositions suitable for peroral (sublingual) administration comprise suckable tablets which contain a compound of the formula (I) with a flavoring, normally sucrose, and gum arabic or tragacanth, and pastilles which contain the compound in an inert base such as gelatin and glycerol or sucrose and gum arabic.

Suitable pharmaceutical compositions for parenteral administration comprise preferably sterile aqueous preparations of a compound of the formula (I), which are preferably isotonic with the blood of the intended recipient. These preparations are preferably administered intravenously, although administration may also take place by subcutaneous, intramuscular or intradermal injection. These preparations may preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These may be produced by mixing a compound of the formula (I) with one or more conventional solid carriers, for example cocoa butter, and shaping the resulting mixture.

The pharmaceutical composition in the inventive method when in the form of a soft gelatin capsule may comprise about 100 mg of a compound of formula (I). The pharmaceutical composition in the inventive method when in the form of an emulsion may comprise about 60 mg of a compound of formula (I). The pharmaceutical composition in the inventive method when in the form of a rectal suppository may comprise about 40 mg of a compound of formula (I). The pharmaceutical composition in the inventive method when in the form of a tablet may comprise about 40 mg of a compound of formula (I). The pharmaceutical composition in the inventive method when in the form of a coated tablet may comprise about 50 mg of a compound of formula (I). The pharmaceutical composition in the inventive method when in the form of a hard gelatin capsule may comprise about 100 mg of a compound of formula (I). The pharmaceutical composition in the inventive method when in the form of liquid drops may comprise about 100 mg of a compound of formula (I) in 1 ml of drops.

Suitable pharmaceutical compositions for topical use on the skin are preferably in the form of an ointment, cream, lotion, paste, spray, aerosol or oil. Carriers which may be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal applications may be in the form of single plasters which are suitable for long-term close contact with the patient's epidermis. Plasters of this type suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. As a particular option, the active ingredient may be released by electrotransport or iontophoresis as described, for example, in Pharmaceutical Research, 2 (6): 318 (1986).

The following preparations serve to illustrate the invention without, however, restricting it.

EXAMPLE A
Soft gelatin capsules containing 100 mg of active ingredient per capsule:

|  | per capsule |
|---|---|
| active ingredient | 100 mg |
| triglyceride mixture fractionated from coconut oil | 400 mg |
| capsule contents | 500 mg |

EXAMPLE B
Emulsion containing 60 mg of active ingredient per 5 ml:

|  | per 100 ml of emulsion |
|---|---|
| active ingredient | 1.2 g |
| neutral oil | q.s. |
| sodium carboxymethylcellulose | 0.6 g |
| polyoxyethylene stearate | q.s. |
| glycerol, pure | 0.2 to 2.0 g |
| flavoring | q.s. |
| water (deionized or distilled) | ad 100 ml |

EXAMPLE C
Rectal drug form containing 40 mg of active ingredient per suppository:

|  | per suppository |
|---|---|
| active ingredient | 40 mg |
| suppository base | ad 2 g |

EXAMPLE D
Tablets containing 40 mg of active ingredient per tablet:

|  | per tablet |
|---|---|
| active ingredient | 40 mg |
| lactose | 600 mg |
| corn starch | 300 mg |
| soluble starch | 20 mg |
| magnesium stearate | 40 mg |
|  | 1000 mg |

EXAMPLE E
Coated tablets containing 50 mg of active ingredient per tablet:

|  | per tablet |
|---|---|
| active ingredient | 50 mg |
| corn starch | 100 mg |
| lactose | 60 mg |
| sec. calcium phosphate | 30 mg |
| soluble starch | 5 mg |
| magnesium stearate | 10 mg |
| colloidal silica | 5 mg |
|  | 260 mg |

EXAMPLE F
The following formulas are suitable for producing the contents of hard gelatin: capsules

| | | |
|---|---|---|
| a) | active ingredient | 100 mg |
| | corn starch | 300 mg |
| | | 400 mg |
| b) | active ingredient | 140 mg |
| | lactose | 180 mg |
| | corn starch | 180 mg |
| | | 500 mg |

EXAMPLE G

Drops may be produced in accordance with the following formula (100 mg of active ingredient in 1 ml 20 drops):

| | |
|---|---|
| active ingredient | 10 g |
| methyl benzoate | 0.07 g |
| ethyl benzoate | 0.03 g |
| ethanol, 96% | 5 ml |
| demineralized water | ad 100 ml |

The invention further relates to a process for preparing the compounds of the formula I, which comprises preparing compounds of the formula I in accordance with the following reaction scheme:

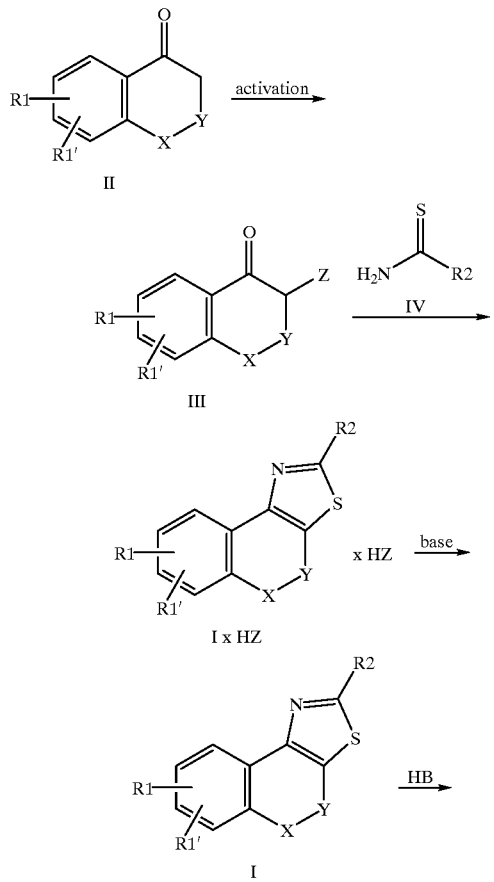

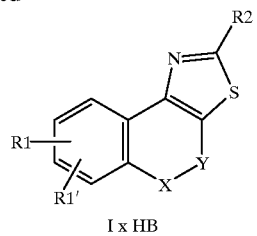

Bicyclic ketones of the formula II in which R1, R1', X and Y have the stated meanings either are commercially available or may be prepared by methods known from the literature.

Bicyclic ketones of the formula II in which R1 or R1' are aryl radicals may be obtained by Pd(0)-catalyzed addition of boronic esters onto compounds of the formula II in which R1 and/or R1' are bromine, iodine or trifluoromethylsulfonyloxy (for example: N. Miyaura and A. Suzuki, Chem. Rev. 95, 2457–83 (1995) or T. Oh-e, N. Miyaura and A. Suzuki, J. Org. Chem. 58, 2201–08 (1993)).

Bicyclic ketones of the formula II in which R1 and/or R1' are alkynyl radicals or alkenyl radicals may be prepared, for example, by methods like those described by K. Sonagashira et al., Tetrahedron Lett. 4467 (1975) and S. Takahashi et al., Synthesis 627 (1980) (palladium-catalyzed reaction of, for example, trimethylsilylacetylene or alkynes) or by E. Negishi et al., J. Org. Chem. 62, 8957–60 (1997) (alkynylzinc bromide) or by A. Hassner et al., J. Org. Chem. 49, 2546 (1984) (trialkylstannylalkynes, trialkylstannylvinyl or allyl compounds, 1-alkenylboron compounds or vinyl compounds).

The bicyclic ketones of the formula II are activated most simply by a reaction with bromine to give the alpha-bromo ketone of the general formula III (Z=Br). Z in the activated compounds of the general formula III may, however, also advantageously be Cl, I, O—C(O)—$C_6H_4$-4-$NO_2$, O—$SO_2$—$CH_3$, O—$SO_2$—$CF_3$, O—$SO_2$—$C_6H_4$-4-$CH_3$ or O—$SO_2$—$C_6H_5$.

Compounds of the formula I×HZ are obtained by reacting thioamides of the formula IV in which R2 has the stated meanings. The procedure for this is advantageously such that the compounds III are reacted with the thioamides IV in the molar ratio of from 1:1 to 1:1.5. The reaction is advantageously carried out in an inert solvent, for example in polar organic solvents such as dimethylformamide, dimethylacetamide, N-methyl-2-pyrrolidone, dioxane, tetrahydrofuran, acetonitrile, nitromethane or diethylene glycol dimethyl ether. However, solvents which prove to be particularly advantageous are methyl acetate and ethyl acetate, short-chain alcohols such as methanol, ethanol, propanol, isopropanol, and lower dialkyl ketones such as, for example, acetone, 2-butanone or 2-hexanone. It is also possible to use mixtures of the reaction media mentioned; thus, it is also possible to use mixtures of the solvents mentioned with solvents which are less suitable on their own, such as, for example, mixtures of methanol with benzene, ethanol with toluene, methanol with diethyl ether or with tert-butyl methyl ether, ethanol with tetrachloromethane, acetone with chloroform, dichloromethane or 1,2-dichloroethane, it being expedient for the more polar solvent in each case to be used in excess. The reactants may be present either in suspension or solution in the particular reaction medium. It is also possible in principle for the reactants to be reacted without a solvent, especially when the particular thioamide has a low melting point. The reaction is only slightly exothermic and may be carried out at between −10° C. and 150° C., preferably between 50° C. and 100° C. A temperature range between 50° C. and 80° C. usually proves to be particularly favorable.

Apart from the derivatives described in the examples, also obtained according to the invention are the compounds of the formula I, and their acid addition products, compiled in the following tables:

TABLE 1

Examples

Formula I

| Example | $R_1$; $R_1'$ | $R_2$ | X | Y | Salt | m.p. [° C.] |
|---|---|---|---|---|---|---|
| 1 | 6-Cl; H | $CH_3$ | — | $CH_2$ | HCl | 227 |
| 2 | 7-($C_6H_4$-4-$CF_3$); H | $CH_3$ | — | $CH_2$ | — | 137 |
| 3 | 5-($C_6H_4$-4-$CF_3$); H | $CH_3$ | — | $CH_2$ | — | 159 |
| 4 | 6-Cl; H | $C(CN)=C(CH_3)_2$ | — | $CH_2$ | — | Decomp. from 32 |
| 5 | 6-Cl; H | $C(O)OCH_2CH_3$ | — | $CH_2$ | — | 162 |
| 6 | 6-Cl; H | $CH_2$—CN | — | $CH_2$ | — | 134 |
| 7 | 6-Cl; H | $CH_3$ | — | $CH_2$ | — | Decomp. from 125 |
| 8 | 6-Cl; H | $C_6H_4$-4-$CF_3$ | — | $CH_2$ | — | 130 |
| 9 | 6-Cl; H | $C_6H_5$ | — | $CH_2$ | — | 106 |
| 10 | 6-($C_6H_4$-4-Cl); H | $CH_3$ | — | $CH_2$ | — | 173 |
| 11 | 6-($C_6H_4$-3-Cl); H | $CH_3$ | — | $CH_2$ | — | 112 |
| 12 | 6-Cl; H | $CH_2$—O—C(O)—$C(CH_3)_3$ | — | $CH_2$ | — | 105 |
| 13 | 6-O—$CH_2$—$CF_3$; H | $CH_3$ | — | $CH_2$ | HBr | 222 |
| 14 | 6-O—$CH_2$—$CF_3$; H | $C_6H_5$ | — | $CH_2$ | HBr | 252 |
| 15 | 6-O—$C_6H_4$-4-Cl; H | $CH_3$ | — | $CH_2$ | HBr | 234 |
| 16 | 6-O—$C_6H_4$-4-Cl; H | $C_6H_5$ | — | $CH_2$ | HBr | 253 |
| 17 | 6-O—$C_6H_4$-3-$CH_3$; H | $C_6H_5$ | — | $CH_2$ | HBr | 271 |
| 18 | 6-O—$C_6H_4$-3-$CH_3$; H | $CH_3$ | — | $CH_2$ | HBr | 240 |
| 19 | 5-Br; H | $C_6H_5$ | $CH_2$ | $CH_2$ | — | 85 |
| 20 | 5,6-di-$CH_3$; H | $CH_3$ | — | $CH_2$ | HBr | 277 |
| 21 | 5,6-di-$CH_3$; H | $C_6H_5$ | — | $CH_2$ | HBr | 290 |
| 22 | 6-Cl; H | $C_6H_4$-4-OH | — | $CH_2$ | — | 280 |
| 23 | 6-Cl; H | $C_6H_4$-2-OH | — | $CH_2$ | — | 198 |
| 24 | 6-Cl; H | Pyrid-3-yl | — | $CH_2$ | — | 169 |
| 25 | 6-Cl; H | $CH_2$-Indol-3-yl | — | $CH_2$ | — | 186 |
| 26 | 6-Cl; H | $CH_2$-benzothiazol-2-yl | — | $CH_2$ | — | 126 |
| 27 | H; H | $CH_3$ | — | $CH_2$ | HCl | 233 |

The reaction time depends substantially on the reaction temperature and is between 2 minutes and 3 days at higher and lower temperatures respectively. In the favorable temperature range, the reaction time is generally between 5 minutes and 48 hours.

The resulting salts of the compounds of the formula I×HZ may be converted with organic or inorganic bases into the free basic compounds of the formula I.

The compounds of the formula I may be converted into their acid addition salts of the formula I×HB by reaction with organic or inorganic acids of the formula HB. Examples of suitable inorganic acids HB are: hydrohalic acids such as hydrochloric acid and hydrobromic acid, and sulfuric acid, phosphoric acid and sulfamic acid. Examples of organic acids HB which may be mentioned are: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethane-sulfonic acid, 1,2-benzisothiazol-3(2H)-one, 6-methyl-1,2,3-oxathiazin-4(3H)-one 2,2-dioxide.

The compounds of the formula I are distinguished by beneficial effects on lipid metabolism, and they are particularly suitable as anorectic agents. The compounds may be employed alone or in combination with other anorectic active ingredients. Further anorectic active ingredients of this type are mentioned, for example, in the Rote Liste, chapter 01 under weight-reducing agents/appetite suppressants. Examples include, but are not limited to, Decorpa© (from Pierre Fabre Pharma, common name, sterculia), Xenical© (from Roche, common name orlistat), Antiadipositum X-112S (from Haenseler, common name, D-norpseudoephedrin-HCl), Fasupond© (from Eu Rho Arzneil, common name, D-norpseudoephedrin-HCl), Mirapront© N (from Mack, Illert., common name, D-norpseudoephedrin-Poly(styrol, divinylbeizol)sulfonate), Regenon© l-retard (from Temmler Pharma, common name, Amfepramon-HCl), Rondimen© (from ASTA Medica AWD, common name, Mefenorex-HCl), Tenuate© Retard (from Artegodan, common name, Amfepramon-HCl), Vita-Schlanktropfen Schuck (from Schuck, common name, D-norpseudoephedrin-HCl), Vencipon© N (from Artesan, common name, Ephedrin-HCl), Cefamadar© (from Cefak, common name Madar D4), and Helianthus tuberosus (Plantina). The compounds are suitable for the prophylaxis and, in particular, for the treatment of obesity. The activity of the compounds has been tested as follows:

Biological Test Model

The anorectic effect was tested on male NMR1 mice. After withdrawal of feed for 24 hours, the test product was administered by gavage. The animals were housed singly and had free access to drinking water and, 30 minutes after administration of the product, they were offered condensed milk. The consumption of condensed milk was determined, and the general behavior of the animals was inspected, every half hour for 7 hours. The measured milk consumption was compared with that of untreated control animals.

TABLE 2

Anorectic effect measured by reduction in the cumulative milk consumption by treated animals compared with untreated animals.

Compound/Example Formula I

| | Oral dose [mg/kg] | Number of animals/ cumulative milk consumption by the treated animals N/[ml] | Number of animals/ cumulative milk consumption by the untreated control animals N/[ml] | Reduction in the cumulative milk consumption as % of the controls |
|---|---|---|---|---|
| Example 5 | 50 | 5/2.26 | 5/4.02 | 44 |
| Example 6 | 50 | 5/2.28 | 5/4.02 | 43 |
| Example 7 | 50 | 5/0.58 | 5/3.44 | 83 |
| Example 11 | 50 | 4/1.58 | 5/3.24 | 51 |
| Example 13 | 50 | 5/1.82 | 5/3.80 | 52 |
| Example 20 | 50 | 5/1.98 | 5/4.06 | 51 |

The examples detailed below serve to illustrate the invention without, however, restricting it. The stated decomposition points are not corrected and generally depend on the heating rate.

PROCEDURE EXAMPLE 1

6-Chloro-2-methyl-8H-indeno[1,2-d]thiazole hydrochloride (Compound of Example 1):

a) 2-Bromo-5-chloroindan-1-one:

5-Chloroindan-1-one is reacted with bromine in glacial acetic acid using a catalytic amount of 48% strength HBr solution in water at room temperature. 2-Bromo-5-chloroindan-1-one is obtained with a melting point of 94–96° C.

b) 6-Chloro-2-methyl-8H-indeno[1,2-d]thiazole hydrochloride:

1 g of 2-bromo-5-chloroindan-1-one is stirred with 0.31 g of thioacetamide in 100 ml of acetone at room temperature for 5 h. The precipitate is filtered off with suction, washed with acetone and dried in vacuo. The hydrobromide is suspended in ethyl acetate and neutralized with triethylamine, and the ethyl acetate solution is washed with water, dried over sodium sulfate, filtered and concentrated in vacuo. The free base is dissolved in tetrahydrofuran, and an excess of ethereal HCl is added to this solution. The mixture is stirred at room temperature for 2 h and then concentrated in vacuo. The residue (hydrochloride of 6-chloro-2-methyl-8,8a-dihydroindeno [1,2-d]thiazol-3a-ol) is heated under reflux in 30 ml of glacial acetic acid for 4 h. The solvent is removed in vacuo, the residue is stirred with diisopropyl ether and 6-chloro-2-methyl-8H-indeno[1,2-d]thiazole hydrochloride is obtained with a melting point of 135° C.

PROCEDURE EXAMPLE 2

(6-Chloro-8H-indeno[1,2-d]thiazol-2-yl)acetonitrile (Compound of Example 6)

1 g (4 mmol) of 2-bromo-5-chloroindan-1-one is stirred with 450 mg (4.5 mmol) of 2-cyanothioacetamide and 0.55 ml (4 mmol) of triethylamine in 10 ml of dry ethanol at room temperature for 4 h. The reaction mixture is concentrated in vacuo, and the residue is purified by chromatography on silica gel with ethyl acetate/n-heptane 1/1. (6-Chloro-8H-indeno[1,2-d]thiazol-2-yl)acetonitrile is obtained with a melting point of 134° C.

PROCEDURE EXAMPLE 3

6-Chloro-2-methyl-8H-indeno[1,2-d]thiazole (Compound of Example 7)

A suspension of the compound of procedure example 1 in ethyl acetate is extracted by shaking several times with a concentrated aqueous sodium bicarbonate solution; the ethyl acetate phase is then dried over sodium sulfate, filtered and concentrated in vacuo. 6-Chloro-2-methyl -8H-indeno[1,2-d]thiazole is obtained with a melting point of 94° C.

PROCEDURE EXAMPLE 4

6-(3–Chlorophenyl)-2-methyl-8H-indeno[1,2-d]thiazole (Compound of Example 11)

a) 5-(3–Chlorophenyl)indan-1-one:

3 g (14.2 mmol) of 5-bromoindan-1-one are suspended with 2.22 g (14.2 mmol) of 3-chlorophenylboronic acid and 3 g (28.3 mmol) of sodium carbonate in a mixture of 100 ml of toluene, 20 ml of ethanol and 20 ml of water. Under an argon atmosphere, 160 mg (7.1 mmol) of palladium(II) acetate and 373 mg (14.2 mmol) of triphenylphosphine are added. The mixture is heated under reflux for 3 h, and then the ethanol content of the solvent mixture is removed in vacuo. 40 ml of 0.5 N sodium hydroxide solution are added, and the mixture is stirred at room temperature for 10 min. The precipitate is filtered off with suction; the filtrate is washed with 40 ml of water until neutral and then washed with concentrated brine (3×40 ml), dried over magnesium sulfate, concentrated in vacuo and purified by chromatography on silica gel with toluene/ethyl acetate 20/1. 5-(3-Chlorophenyl)indan-1-one is obtained with a melting point of 113° C.

b) 2-Bromo-5-(3-chlorophenyl)indan-1-one:

2.42 g (10 mmol) of 5-(3-chlorophenyl)indan-1-one are dissolved in 30 ml of glacial acetic acid and, after addition of 10 µof a 48% strength HBr solution in water, treated dropwise while stirring with a solution of 0.77 ml (15 mmol) of bromine in 7 ml of glacial acetic acid. After the reaction mixture has been stirred at room temperature for 3 h, it is poured into a mixture of 100 g of ice with 70 ml of water and 100 mg of NaHSO$_3$ and stirred. The resulting suspension is extracted by shaking with 200 ml of dichloromethane, and the organic phase is then washed with water (3×100 ml), dried over magnesium sulfate, concentrated in vacuo and purified by chromatography on silica gel with toluene/ethyl acetate 50/1. 2-Bromo-5-(3-chlorophenyl)indan-1-one is obtained with a melting point of 110° C., in addition to a little 2,2-dibromo-5-(3-chlorophenyl)indan-1-one.

c) 6-(3–Chlorophenyl)-2-methyl-8H-indeno[1,2-d]thiazole:

321 mg of 2-bromo-5-(3-chlorophenyl)indan-1-one are dissolved with 83 mg of thioacetamide in 10 ml of dry acetone and stirred at 0° C. for 5 h. The precipitate consisting of 6-(3-chlorophenyl)-2-methyl-8,8a-dihydroindeno[1,2-d]thiazol-3a-ol hydrobromide is filtered off with suction, washed with acetone, dried in vacuo and then dissolved in 20 ml of dry methanol. The solution is left to stand at room temperature for 2 weeks. It is made basic with triethylamine, concentrated and purified on silica gel with ethyl acetate/n-heptane 1/1. 6-(3-Chlorophenyl)-2-methyl-8H-indeno[1,2-d]thiazole is obtained with a melting point of 111–112° C. in addition to 6-(3-chlorophenyl)-3a-methoxy-2-methyl-8,8a-dihydro-3aH-indeno[1,2-d]thiazole with a melting point of 80–82° C.

PROCEDURE EXAMPLE 5

2-Methyl-6-(2,2,2-trifluoroethoxy)indeno[1,2-d]thiazole hydrobromide (Compound of Example 13):

a) 5-(2,2,2-Trifluoroethoxy)indan-1-one:

2.2 ml of 2,2,2-trifluoroethanol are added to a stirred mixture of 3.5 g of 5-fluoroindan-1-one, 20 ml of anhydrous dimethylformamide and 4.1 g of anhydrous and ground potassium carbonate and stirred at 80° C. for 10 hours. The solvent is removed by distillation under reduced pressure, the residue is dissolved in ethyl acetate, and the organic phase is washed several times with water. The indanone derivative is obtained as a brownish crystalline solid after chromatography on silica gel with a mixture of equal parts of ethyl acetate and toluene as eluent. Melting point 93–97° C.

b) 2-Bromo-5-(2,2,2-trifluoroethoxy)indan-1-one:

This compound is obtained by reacting 0.9 g of 5-(2,2,2-tri-fluoroethoxy)indan-1-one with 0.2 ml of bromine in 25 ml of ethyl acetate. The compound is used further without further purification.

c) 2-Methyl-6-(2,2,2-trifluoroethoxy)indeno[1,2-d]thiazole hydrobromide:

2-Bromo-5-(2,2,2-trifluoroethoxy)indan-1-one is stirred with an equivalent amount of thioacetamide in acetone at room temperature for 5 h. The precipitate consisting of 2-methyl-6-(2,2,2-trifluoroethoxy)-8,8a-dihydroindeno[1,2-d]thiazol-3a-ol hydrobromide is removed and boiled in 15 ml of glacial acetic acid. The solvent is removed by distillation under reduced pressure, and the residue is induced to crystallize under diisopropyl ether. Colorless crystals, melting point 220–224° C.

PROCEDURE EXAMPLE 6

8-Bromo-2-phenyl-4,5-dihydronaphtho[1,2-d]thiazole (Compound of Example 19)

0.3 g of 2,7-dibromo-3,4-dihydro-2H-naphthalen-1-one is dissolved in 10 ml of ethanol and, after addition of 140 mg of thiobenzamide, heated to reflux for 5 h. The reaction mixture is concentrated in vacuo, the residue is suspended in 10 ml of 1 N sodium hydroxide solution and stirred at room temperature for 1 h. The suspension is filtered with suction, thoroughly washed with water and dried in vacuo. 8-Bromo-2-phenyl-4,5-dihydronaphtho[1,2-d]thiazole is obtained with a melting point of 85° C.

PROCEDURE EXAMPLE 7

2,5,6-Trimethyl-8H-indeno[1,2-d]thiazole hydrobromide (Compound of Example 20)

5,6-Dimethylindan-1-one is converted as described above for the other indan-1-ones into 2-bromo-5,6-dimethylindan-1-one. This is reacted with an equivalent amount of thioacetamide in acetone. The precipitate consisting of the hydrobromide of 2,5,6-trimethyl-8,8a-dihydroindeno-[1,2-d]thiazol-3a-ol is heated in glacial acetic acid and affords, after removal of the solvent and treatment with diisopropyl ether, 2,5,6-trimethyl-8H-indeno[1,2-d]thiazole hydrobromide with a melting point of 290° C.

Inventors hereby incorporate by reference in its entirety the priority application DE 19908535.8, filed Feb. 26, 1999.

What is claimed is:

1. A method for the treatment of obesity comprising administering to a patient in need thereof an obesity treating effective amount of a pharmaceutical composition comprising a compound of formula I

I in which

Y is CH$_2$ or CH$_2$—CH$_2$;

X is a direct linkage, CH$_2$, O, NR3 or S;

R1, R1' are independently H, F, Cl, Br, I, CF$_3$, CN, COOH, COO(C$_1$–C$_6$)alkyl, CONH$_2$, CONH(C$_1$–C$_6$)alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, OCF$_3$, O—(C$_2$–C$_6$)-alkyl (where one, more than one or all hydrogen(s) in the alkyl, alkenyl and alkynyl radicals may be replaced by fluorine, or one hydrogen may be replaced by OH, CN, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO$_2$—(C$_1$–C$_6$)- alkyl, SO—(CH$_2$)-phenyl, SO$_2$—(CH$_2$)$_n$-phenyl (where n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6 ), 1- or 2-naphthyl, 2-, 3- or 4-pyridyl, 2- or 3-furanyl or 2- or 3-thienyl (wherein the phenyl, biphenylyl, naphthyl, pyridyl, furanyl or thienyl rings may be optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is (C$_1$–C$_8$)-alkyl, (C$_3$–C$_7$)-cycloalkyl, (C$_2$–C$_6$)-alkenyl, (C$_2$–C$_6$)-alkynyl, C(CN)=C(CH$_3$)$_2$, C(O)OCH$_2$CH$_3$, CH$_2$—O—C(O)—C(CH$_3$)$_3$, (C$_4$–C$_7$) cycloalkenyl (where one, more than one or all hydrogen(s) in the alkyl, alkenyl or alkynyl radicals may be replaced by fluorine, or one hydrogen may be replaced by OH, CN or O—(C$_1$–C$_4$)-alkyl), (CH$_2$)$_n$-NR6R7 (where n is 1–6 and R6 and R7 are independently H, (C$_1$–C$_6$)-alkyl, (C$_3$–C$_6$)-cycloalkyl, CO—(C$_1$–C$_6$)-alkyl, CHO or CO-phenyl or -NR6R7 is a ring selected from the group consisting of pyrrolidine, piperidine, morpholine, piperazine, 4-methylpiperazin-1-yl, 4-benzylpiperazin-1-yl and phthalimidyl) or (CH$_2$)$_n$-aryl (where n is 0–6 and aryl is selected from the group consisting of phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 1,3,5-triazin-2-yl, 2- or 5-benzimidazolyl, 2-benzothiazolyl, 1,2,4-triazol-3-yl, 1,2,4-triazol-5-yl, tetrazol-5-yl, indol-3-yl, indol-5-yl and N-methylimidazol-2-, -4- or -5-yl wherein the aryl radical or heteroaryl radical may be substituted up to two times by F, Cl, Br, OH, CF$_3$, NO$_2$, CN, OCF$_3$, O—(Cl$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$) cycloalkyl, CONH$_2$, CONH(C$_1$–C$_6$)alkyl, CON[(C$_1$–C$_6$)alkyl]$_2$, CONH(C$_3$–C$_6$)cycloalkyl, NH$_2$, NH—CO—(C$_1$–C$_6$)-alkyl, NH—CO-phenyl, pyrrolidin-1-yl, morpholin-1-yl, piperidin-1-yl, piperazin-1-yl, 4-methylpiperazin-1-yl, (CH$_2$)$_n$-phenyl, O—(CH$_2$)$_n$-phenyl, S—(CH$_2$)$_n$-phenyl or SO$_2$—(CH$_2$)$_n$-phenyl, where n=0–3);

R3 is H, (C$_1$–C$_6$)-alkyl, CO—(C$_1$–C$_5$)-alkyl, CO—(C$_3$–C$_6$)-cycloalkyl, SO$_2$-phenyl or p-toluenesulfonyl; and their physiologically tolerated salts and physiologically functional derivatives.

2. The method of claim 1, wherein

Y is CH$_2$;

X is a direct linkage or CH$_2$;

R1, R1' are independently H, F, Cl, Br, I, CF$_3$, CN, COOH, COO(C$_1$–C$_6$)alkyl, CONH$_2$, CONH(C$_1$–C$_6$) alkyl, CON[(C$_1$–C$_6$)alkyl]$_2$ (C$_1$–C$_6$)-alkyl, (C$_2$–C$_6$)-alkenyl, (C$_2$–C$_6$)-alkynyl, OCF$_3$, O—(C$_2$–C$_6$)-alkyl (where one, more than one or all hydrogen(s) in the alkyl, alkenyl and alkynyl radicals may be replaced by fluorine, or one hydrogen may be replaced by OH, CN, NH$_2$), NH$_2$, NH—(C$_1$–C$_6$)-alkyl, N((C$_1$–C$_6$)-alkyl)$_2$, phenyl, O—(CH$_2$)$_n$-phenyl (where n is 0–6 ), 1- or 2-naphthyl, 2-, 3- or 4-pyridyl, 2- or 3-furanyl or 2- or 3-thienyl (wherein the phenyl, naphthyl, pyridyl, furanyl or thienyl rings may be optionally substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$);

R2 is (C$_1$–C$_8$)-alkyl, (C$_3$–C$_7$)-cycloalkyl, (C$_2$–C$_6$)-alkenyl, (C$_2$–C$_6$)-alkynyl, C(CN)=C(CH$_3$)$_2$, C(O)OCH$_2$CH$_3$, CH$_2$—O—C(O)—C(CH$_3$)$_3$, (C$_4$–C$_7$)-cycloalkenyl (where one, more than one or all hydrogen(s) in the alkyl, alkenyl or alkynyl radicals may be replaced by fluorine, or one hydrogen may be replaced by OH, CN or O—(C$_1$–C$_4$)-alkyl), (CH$_2$)$_n$-NR6R7 (where n is 1–6 and R6 and R7 are independently H, (C$_1$–C$_6$)-alkyl, (C$_3$–C$_6$)-cycloalkyl, CO—(C$_1$–C$_6$)-alkyl, CHO or CO-phenyl), (CH$_2$)$_n$-aryl (where n is 0–6 and aryl is selected from the group consisting of phenyl, biphenylyl, 1- or 2-naphthyl, 2-, 3- or 4-pyridyl, benzothiazol-2-yl, indol-3-yl, indol-5-yl, 2- or 3-furanyl and 2- or 3-thienyl, wherein the phenyl, biphenylyl, naphthyl, pyridyl, furanyl or thienyl rings may be independently substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), and their physiologically tolerated salts and physiologically functional derivatives.

3. The method of claim 1, wherein:

Y is —CH$_2$—;

X is —CH$_2$—, or a direct linkage;

R1 is Cl, Br, (C$_1$–C$_6$)-alkyl, OCF$_3$, O—(C$_2$–C$_6$)-alkyl (where one, more than one or all hydrogen(s) in the alkyl radicals may be replaced by fluorine) or phenyl (which may be substituted up to 3 times by F, Cl, Br, OH or (C$_1$–C$_6$)-alkyl);

R1' is H or R1;

R2 is (C$_1$–C$_6$)-alkyl, (C$_1$–C$_6$)-alkyl-CN, C(CN)=C(CH$_3$)$_2$, C(O)OCH$_2$CH$_3$, CH$_2$—O—C(O)—C(CH$_3$)$_3$,(CH$_2$)$_n$-aryl (where n is 0–2, and aryl is selected from the group consisting of phenyl, 2-, 3- or 4-pyridyl, benzothiazol-2-yl, indol-3-yl and indol-5-yl, wherein the aryl radical or heteroaryl radical may be substituted up to two times by F, Cl, Br, OH, CF$_3$, NO$_2$, CN, OCF$_3$, (C$_1$–C$_6$)-alkyl or O—(C$_1$–C$_6$)-alkyl);

and their physiologically tolerated salts.

4. The method of claim 1, further comprising administering one or more anorectic active ingredients.

5. The method of claim 2, further comprising administering one or more anorectic active ingredients.

6. The method of claim 3, further comprising administering one or more anorectic active ingredients.

7. The method of claim 1, wherein the pharmaceutical composition comprises a dose in the range of 0.3 mg to 100 mg.

8. The method of claim 7, wherein the pharmaceutical composition comprises a dose in the range of 3 mg to 50 mg.

9. The method of claim 1, wherein the pharmaceutical composition is in the form of a soft gelatin capsule.

10. The method of claim 9, wherein the soft gelatin capsule comprises 100 mg of a compound of formula (I).

11. The method of claim 1, wherein the pharmaceutical composition is in the form of an emulsion.

12. The method of claim 11, wherein the emulsion comprises 60 mg of a compound of formula (I) per 5 ml dose.

13. The method of claim 1, wherein the pharmaceutical composition is in the form of a rectal suppository.

14. The method of claim 13, wherein the rectal suppository comprises 40 mg of a compound of formula (I).

15. The method of claim 1, wherein the pharmaceutical composition is in the form of a tablet.

16. The method of claim 15, wherein the tablet comprises 40 mg of a compound of formula (I).

17. The method of claim 1, wherein the pharmaceutical composition is in the form of a coated tablet.

18. The method of claim 17, wherein the coated tablet comprises 50 mg of a compound of formula (I).

19. The method of claim 1, wherein the pharmaceutical composition is in the form of a hard gelatin capsule.

20. The method of claim 19, wherein the hard gelatin capsule comprises 100 mg of a compound of formula (I).

21. The method of claim 1, wherein the pharmaceutical composition is in the form of liquid drops.

22. The method of claim 21, wherein the liquid drops comprises 100 mg of a compound of formula (I) in 1 ml of drops.

* * * * *